(12) United States Patent
Hasegawa et al.

(10) Patent No.: US 6,966,977 B2
(45) Date of Patent: Nov. 22, 2005

(54) BIOSENSOR

(75) Inventors: Miwa Hasegawa, Hyogo (JP);
Tomohiro Yamamoto, Hirakata (JP);
Motokazu Watanabe, Toyonaka (JP);
Shin Ikeda, Katano (JP); Shiro Nankai, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 406 days.

(21) Appl. No.: 10/350,139

(22) Filed: Jan. 24, 2003

(65) Prior Publication Data

US 2003/0132110 A1 Jul. 17, 2003

Related U.S. Application Data

(63) Continuation of application No. PCT/JP01/06471, filed on Jul. 26, 2001.

(30) Foreign Application Priority Data

Jul. 31, 2000 (JP) .............................. 2000-232385
Aug. 3, 2000 (JP) .............................. 2000-236131

(51) Int. Cl.$^7$ .......................................... G01N 27/327
(52) U.S. Cl. ........................ 204/403.07; 204/403.06; 204/403.05
(58) Field of Search .................. 204/403.05, 403.09, 204/403.1, 403.11, 403.14, 403.06, 403.07

(56) References Cited

U.S. PATENT DOCUMENTS

| | | | |
|---|---|---|---|
| 4,477,575 A | 10/1984 | Vogel et al. | 436/170 |
| 5,609,749 A | 3/1997 | Yamauchi et al. | 205/777.5 |
| 5,658,444 A | 8/1997 | Black et al. | |

FOREIGN PATENT DOCUMENTS

| | | |
|---|---|---|
| EP | 0 663 446 A2 | 7/1995 |
| EP | 0 045 476 A1 | 2/1998 |
| EP | 0 856 586 A1 | 8/1998 |
| EP | 1 235 068 A1 | 8/2002 |
| JP | 63-58149 | 3/1988 |
| JP | 2-62952 | 3/1990 |
| JP | 7-234201 | 9/1995 |
| JP | 8-54387 | 2/1996 |
| JP | 9-318588 | 12/1997 |
| JP | 11-344461 | 12/1999 |
| WO | WO 01/36954 A1 | 5/2001 |

OTHER PUBLICATIONS

"Electrochemical Diagnostic Strip Device for Total Cholesterol and Its Subfractions", R. Foster et al., Electroanalysis 2000, vol. 12, No. 9, pp. 716-721, 2000.

*Primary Examiner*—Alex Noguerola
(74) *Attorney, Agent, or Firm*—McDermott Will & Emery LLP

(57) ABSTRACT

A sensor including an insulating base plate; an electrode system, provided on the base plate, having a measuring electrode and a counter electrode; a reaction layer including at least an oxidoreductase and an electron mediator; a sample solution supply pathway including the electrode system and the reaction layer; and a sample supply unit, wherein the sensor is so structured that, between the sample supply unit and the sample solution supply pathway, there is provided a filter having a function to filter out hemocytes and having a cross-sectional area larger than an opening of the sample solution supply pathway, and that plasma of a blood with hemocytes thereof having been filtered out is sucked into the inside of the sample solution supply pathway owing to capillary phenomena.

9 Claims, 11 Drawing Sheets

(a)

(b)

(c)

(a)

(b)

(c)

(a)

(b)

F I G. 1 3
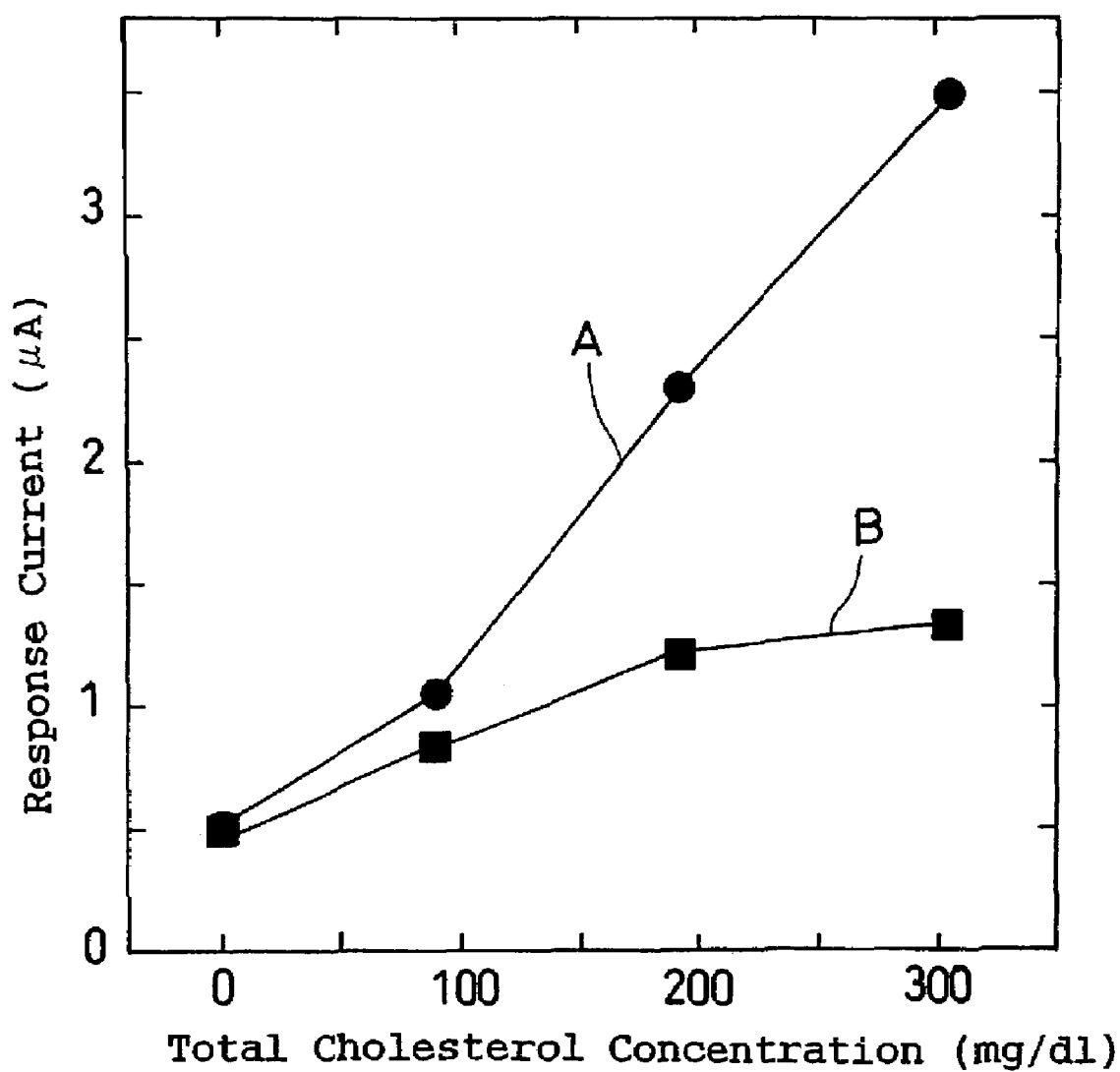

BIOSENSOR

This application is a continuation of PCT/JP01/06471 filed on Jul. 26, 2001.

TECHNICAL FIELD

The present invention relates to a biosensor, particularly to a cholesterol sensor, that can easily quantify a specific component in a sample at a high speed and a high accuracy.

BACKGROUND ART

As one example of conventional biosensors, a glucose sensor will be described below.

A generally known method of quantifying glucose is a system using a combination of glucose oxidase with an oxygen electrode or a hydrogen peroxide electrode. Glucose oxidase selectively oxidizes β-D-glucose, as a substrate, to D-glucono-δ-lactone, using oxygen as an electron mediator. During this reaction process, oxygen is reduced to hydrogen peroxide. Here, glucose is quantified either by measuring an amount of consumed oxygen with use of the oxygen electrode, or by measuring an amount of generated hydrogen peroxide with use of e.g. a platinum electrode.

However, such methods as described above are much influenced by dissolved oxygen concentration in the case of certain objects to be measured, or are impossible under conditions of oxygen being absent. Thus, a glucose sensor of such type has been developed that uses, as the electron mediator, a metal complex or an organic compound such as potassium ferricyanide, a ferrocene derivative and a quinone derivative without using oxygen as the electron mediator (See Japanese Laid-open Patent Publication Hei 2-062952).

For making this biosensor, an electrode system comprising a measurement electrode, a counter electrode, and a reference electrode is formed on an insulating base plate by e.g. screen printing, and an enzyme reaction layer including a hydrophilic polymer, an oxidoreductase, and an electron mediator is then formed on the electrode system. In case of need, a buffer is further added to this enzyme reaction layer.

When a sample solution containing the substrate is dropped onto the enzyme reaction layer of this biosensor, the enzyme reaction layer gets dissolved, and the enzyme reacts with the substrate, whereby this reaction causes the electron mediator to get reduced. The concentration of the substrate in the sample solution can be determined by an oxidation current for electrochemically oxidizing the thus reduced electron mediator after the end of the enzyme reaction.

According to this type of sensor, the reduced form of the electron mediator generated in consequence of the enzyme reaction is oxidized by the electrode, and the concentration of glucose can be determined by the oxidation current.

Such a biosensor can be used, in principle, for measuring various substances by using an enzyme whose substrate is each of the substances to be measured. For example, a serum cholesterol level, which is used as a diagnostic index in various medical institutions, can be measured by using, as oxidoreductase, cholesterol oxidase or cholesterol dehydrogenase and cholesterol esterase.

The enzyme reaction of cholesterol esterase progresses very slowly. By adding an appropriate surfactant thereto, cholesterol esterase can be enhanced in its activity, thereby to be able to shorten time needed for total reaction.

However, since this causes the reaction system to contain a surfactant, which badly affects hemocytes, it has been impossible to perform measurements using a whole blood.

As described above, in the case of measuring a cholesterol level in a blood, a surfactant is contained in the reaction system, and the surfactant badly affects erythrocytes in the blood. This has caused it impossible for sensors such as glucose sensors to measure a whole blood per se. A proposal has thus been made to provide a filter member in the vicinity of an opening of a sample solution supply pathway in order to supply thereto only plasma of a blood, with the erythrocytes having been filtered out. However, the speed of the flow of the filtrated plasma into inside of the sensor is low and inconstant, so that response values vary, and that bubbles are often generated when the plasma enters inside of the sensor, whereby measurement has been impossible.

An object of the present invention is to provide a so improved biosensor that does not have above described drawbacks, and allows plasma of a blood, with hemocytes thereof having been filtered out, to quickly reach the electrode system.

Another object of the present invention is to provide a cholesterol sensor, which is highly accurate and has superior response characteristics, and which allows a whole blood to be an object to be measured.

DISCLOSURE OF INVENTION

A biosensor according to the present invention comprises: an insulating base plate; an electrode system having a measuring electrode and a counter electrode provided on the base plate; a reaction layer comprising at least an oxidoreductase and an electron mediator; a sample solution supply pathway including the electrode system and the reaction layer; a sample supply unit; and a filter provided between the sample supply unit and the sample solution supply pathway for filtering out hemocytes of a blood, wherein plasma of the blood, with the hemocytes having been filtered out by the filter, is sucked into inside of the sample solution supply pathway owing to capillary phenomena, characterized in that the filter has, at an upstream side thereof, a cross-sectional area larger than a cross-sectional area of an opening of the sample solution supply pathway.

The filter used here comprises a porous body having pores interconnected in a three-dimensional manner. This porous body moves a blood, owing to capillary action, from the sample supply unit side to the sample solution supply pathway side, and has a function to filter out hemocytes owing to differences in flow resistances between the plasma and the hemocytes. Materials to be used for this filer are nonwoven fabrics, filter papers and other porous bodies, which comprise fibers, preferably hydrophilic fibers, such as glass fiber, cellulose and pulp.

A cross-sectional area of the filter at its upstream side is preferred to be equal to or larger than a cross-sectional area thereof at its downstream side, which is positioned at the opening of the sample solution supply pathway.

BRIEF DESCRIPTION OF DRAWINGS

FIG. 13 is a graph, showing response characteristics of cholesterol sensors according to an Example of the present invention and the Comparative Example.

BEST MODE FOR CARRYING OUT THE INVENTION

Figure 1:
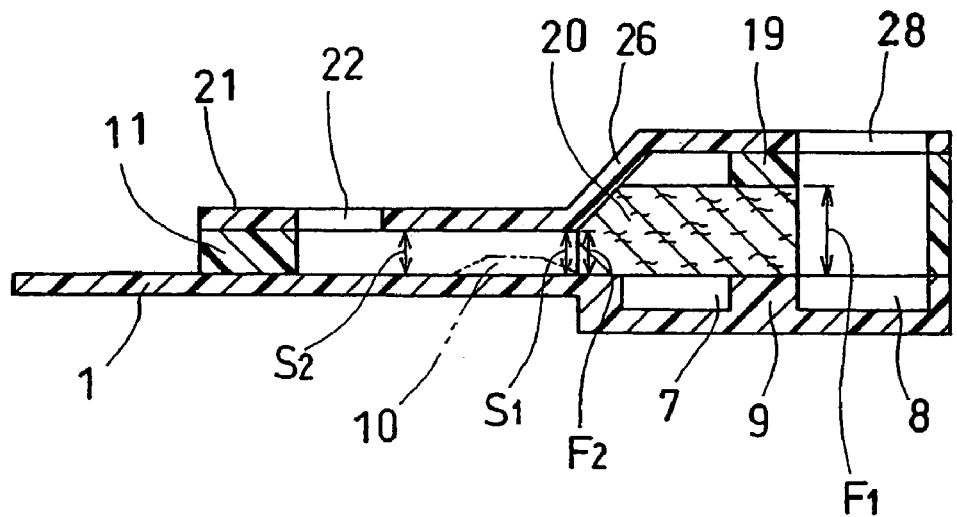
FIG. 1 is a vertical cross-sectional view of a biosensor according to an embodiment mode of the present invention.

As describe above, the present invention is to remove, by use of a filter, hemocytes of a blood that are obstructing substances, and to allow plasma of the blood to quickly flow into an electrode system of a sensor. More specifically, a filter is provided between a sample supply unit and a sample solution supply pathway, which includes an electrode system and a reaction layer, wherein the filter has a function to filter out hemocytes and has a cross-sectional area at an upstream side thereof which is larger than a cross-sectional area of an opening of the sample solution supply pathway. Thereby, the plasma of the flood, with the hemocytes thereof having been filtered out by the filter, is sucked into inside of the sample solution supply pathway owing to capillary phenomena.

According to a preferable embodiment mode, the sample solution supply pathway is formed between the base plate and a cover member combined with the base plate.

According to another preferable embodiment mode, at least a portion of the cover member, which portion is to cover the filter and the sample solution supply pathway, is transparent.

Further, the following conditions are preferred to be satisfied in order to introduce, into the electrode system, the plasma of the blood with the hemocytes having been separated:

1) The cross-sectional area of the sample solution supply pathway is equal to or smaller than the cross-sectional area of the opening of the sample solution supply pathway;

2) The cross-sectional area of the end portion of the filter at the electrode side is equal to or smaller than the cross-sectional area at the sample solution introduction side, i.e. the upstream side thereof; and 3) The filter is supported by a supporting body so as not to be hindered from expansion thereof.

More specifically, it is most preferable that the cross-sectional areas of a hollow portion and the filter within the sensor, where the sample solution flows, decrease gradually from the upstream side of the filter, which faces the sample supply unit, to the air vent side, which is open at the end of the sample solution supply pathway.

Examples of filters having smaller cross-sectional areas at front ends thereof at the electrode side are e.g. those having shapes, as whole filter shapes, of e.g. convex, cone and trapezoid.

What is meant by a smaller cross-sectional area at a front end of a filter is that a part, which supports the front end portion of the filter at the electrode side, becomes narrower as it gets closer to the sample solution supply pathway.

In order to completely remove the hemocytes, which are obstructing substances, it is preferable that there is at least one portion of the filter where the filter is out of contact with a filter-supporting unit within a region spanning from the sample supply unit to the sample solution supply pathway, namely a portion of the filter where a space encircles the surface of the filter, so that the sample solution passes through the filter without exception and fail. Otherwise, there is a possibility that some hemocytes may run along the filter-supporting unit without passing through the filter, and may flow into the electrode system.

Now, let us compare the case, where the filter has, at the downstream thereof, a cross-sectional area smaller than the cross-sectional area at the upstream side thereof, with the case where the filter has one same cross-sectional area from the upstream side to the downstream side. In the former case, the hemocyte separation position is closer to the upstream side as compared with the latter case where the hemocyte separation position is closer to the downstream side. Accordingly, in the latter case, some hemocytes may possibly get into the sample solution supply pathway.

Using these structures and configurations, it is possible to remove obstructing substances in the sample solution, and to allow plasma to quickly flow into the inside of the sensor.

With respect to the relative position between the front end of the filter at the electrodes side and the electrodes, it is preferable that the filter is out of contact with the electrodes.

With respect to a position where to connect the filter member to the electrode type biosensor at, it is ordinarily good to choose such position at the opening side of the sample solution supply pathway, but such position can also be chosen at the air vent side for the purpose of space-saving. In such case, the opening of the sample solution supply pathway functions as an air vent.

The filter-supporting unit such as the cover and the spacer is preferred to be transparent. This is because visual inspection can be made as to the process in which the sample solution is filtered by use of the filter, and the process in which the filtrated sample solution is sucked into inside of the sample solution supply pathway owing to capillary phenomena, whereby it can be confirmed whether the filtration is being successfully done.

Usable electron mediators are potassium ferricyanide and those selected from redox compounds having a function to transfer electrons to and from an oxidoreductase such as cholesterol oxidase.

An oxidoreductase to be used is an enzyme whose substrate is an objective substance to be measured. In the case of the sensor for measuring glucose as an object to be measured, glucose oxidase is to be used.

Cholesterol oxidase or cholesterol dehydrogenase, which is an enzyme for catalyzing oxidation reaction of cholesterol, and cholesterol esterase, which is an enzyme for catalyzing a process of converting cholesterol ester to cholesterol are used for measuring a cholesterol level, used as a diagnosis index, in serum of a blood. The enzyme reaction of cholesterol esterase progresses very slowly. By adding an appropriate surfactant thereto, cholesterol esterase can be enhanced in its activity, thereby to be able to shorten time needed for total reaction. These are placed on or in the vicinity of the electrode system. In the case of a sensor having a cover member which, by being combined with a base plate, forms a sample solution supply pathway between the cover member and the base plate, they can also be provided at a portion exposed to the sample solution supply pathway or at an opening of the sample solution supply pathway. Wherever such position may be, it is preferable that a reaction reagent layer can be easily dissolved by an introduced sample solution thereby to reach the electrode system. In order to protect the electrode and to suppress exfoliation of a formed reaction layer, a hydrophilic polymer layer is preferred to be formed in contact with the surface of the electrode system. Furthermore, other than the electrode system as well, it is preferred that a hydrophilic polymer layer is formed as a base for forming a reaction layer, or that a reaction layer, as a lowermost layer, contains a hydrophilic polymer.

A layer containing an electron mediator is preferred to be separated from a surfactant for the purpose of increasing solubility thereof. Further, it is preferred to be separated from cholesterol esterase, which is an enzyme for catalyzing oxidation reaction of cholesterol, for the purpose of securing stability of storage thereof.

In the case of biosensors for measuring blood sugar levels, there is an example in which a layer, containing a lipid, is formed to cover e.g. a layer formed on the electrode system for the purpose of facilitating introduction of the sample solution to the reaction layer (See e.g. Japanese Laid-open Patent Publication Hei 2-062952). A biosensor for measuring cholesterol according to the present invention contains a surfactant, which has a function similar to that of a lipid, so that it does not need a lipid layer.

Usable hydrophilic polymers are e.g. water-soluble cellulose derivatives, particularly ethyl cellulose, hydroxypropyl cellulose and carboxymethyl cellulose as well as polyvinylpyrrolidone, polyvinyl alcohol, gelatin, polyacrylic acids and their salts, starch and its derivatives, polymer of maleic anhydride and its salts, polyacrylamide, methacrylate resin and poly-2-hydroxyethyl methacrylate.

Surfactants can be selected from n-octyl-β-D-thioglucoside, polyethylene glycol monododecyl ether, sodium cholate, dodecyl-β-maltoside, sucrose monolaurate, sodium deoxycholate, sodium taurodeoxycholate, N,N-bis(3-D-gluconamidepropyl)deoxycholeamide and polyoxyethylene (10)octylphenyl ether.

Lipids to be used are phospholipids, preferably amphipathic lipids, such as lecithin, phosphatydyl choline and phosphatydylethanolamine.

As methods for measuring an oxidation current, there are a two-electrode system using only a measuring electrode and a counter electrode, and a three-electrode system additionally using a reference electrode. The three-electrode system enables more accurate measurements.

Hereinafter, the present invention will be described in more detail with reference to specific embodiment modes.

Figure 2:
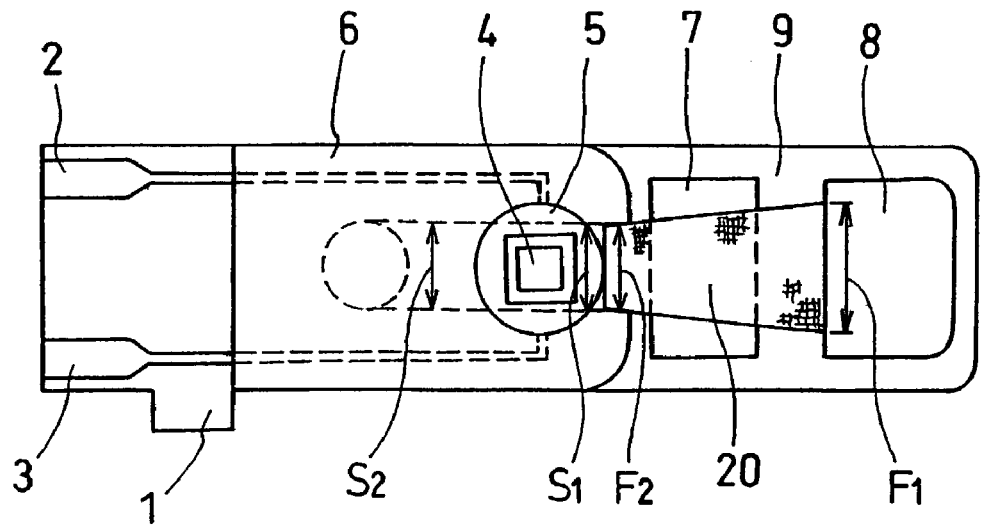
FIG. 2 is a plan view of the same sensor, with a reaction layer, a spacer and a cover having been removed.
Figure 3:
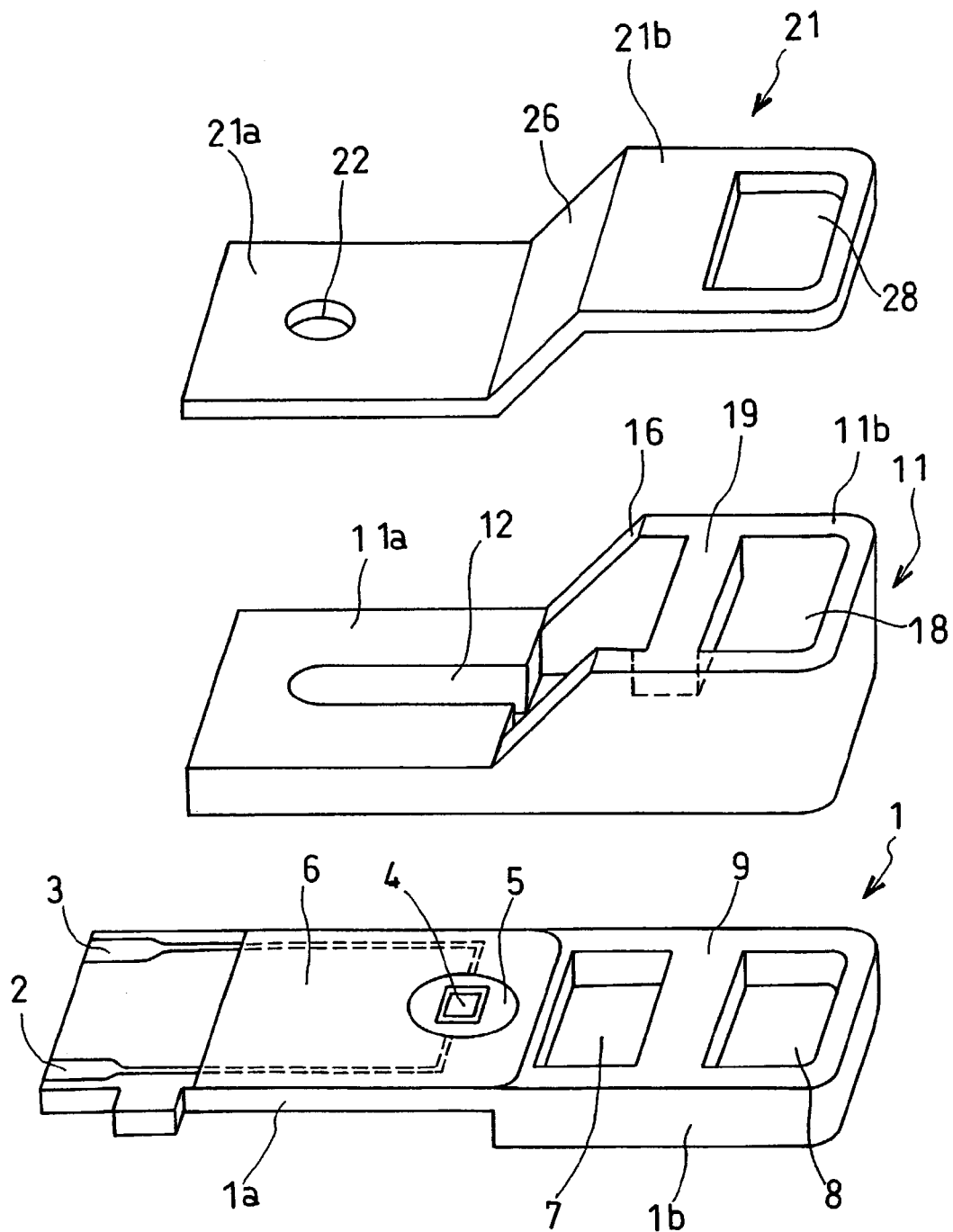
FIG. 3 is an exploded oblique view of the same sensor.

FIG. 1 is a vertical cross-sectional view of a biosensor according to one embodiment mode, and FIG. 2 is a plan view with its reaction layer, spacer and cover having been removed, while FIG. 3 is an exploded oblique view of the biosensor with its reaction layer and filter having been removed.

Reference numeral 1 designates an insulating base plate made of polyethylene terephthalate. This base plate 1 has a left half member 1a with a smaller thickness, and a right half member 1b with a thickness of about twice the thickness of the left half member. On the thinner member 1a, a silver paste is printed to form leads 2, 3 and a base for an electrode system. On the base plate 1, furthermore, an electrically conductive carbon paste containing a resin binder is printed to form an electrode system comprising a measuring electrode 4 and a counter electrode 5. Further, an insulating layer 6 is formed by printing an insulating paste on a certain region. The insulating layer 6 so defines exposed portions of the measuring electrode 4 and the counter electrode 5 as to be constant, and partially covers the leads 2 and 3. At the thicker member 1b of the base plate 1, upwardly open recesses 7 and 8 are provided.

A spacer 11 to be combined with the base plate 1 comprises a flat plate member 11a having a size for substantially covering the insulating layer 6 of the base plate 1, and a roughly U-shaped member 11b having a greater height for covering a peripheral portion of the member 1b of the base plate and for forming a space portion to contain a later described filter on the base plate 1. The U-shaped member 11b has, at a left end portion 16 thereof, a taper to continuously decrease its height so as to have the same height as that of the flat plate member at a section thereof to be connected to the flat plate member 11a. Furthermore, the U-shaped member 11b has a pressing portion 19, to press the filter, at a position above a portion corresponding to a partition portion 9 between the recesses 7 and 8 of the base plate 1. The flat plate member 11a has a slit 12 which penetrates from upside to downside thereof, and which is open to the U-shaped member side.

A cover 21 has members 21a and 21b which respectively cover the flat plate member 11a and the member 11b of the spacer 11, and has, at the member 21b thereof, a slope portion 26 sloping in correspondence with the taper portion 16 of the spacer. The cover 21 further has an air vent 22 to be connected to an end of the slit 12 of the base plate 1, and has a through-hole 28 to be connected to the recess 8 and an opening portion 18 at the right hand side of the pressing portion 19 of the spacer 11.

A biosensor as shown in FIG. 1 is made by: forming a reaction reagent layer or layers on the base plate 1 and/or at the cover 11 side; further setting a filter 20 on the base plate 1; and combining the spacer 11 and the cover 21 with the base plate 1. In FIG. 1, reference numeral 10 designates an electrode system. The filter 20 is fixed in such a way as: to be sandwiched at an upside and a downside of a rear end thereof by the partition portion 9 of the base plate 1 and the pressing portion 19 of the cover 21; and also to be sandwiched at a front end thereof by the slope portion 26 of the cover 21 and a portion of the base plate 1, respectively, the portion of the base plate being contiguous to an opening of a sample solution supply pathway thereof. Furthermore, the filter 20 faces, at a front end thereof, the sample solution supply pathway formed at the slit 12 portion of the spacer 11.

The thus fixed filter 20 does not contact either the base plate or the cover member at an encircling surface thereof positioned above the recess 7 of the base plate 1. Thus, the point is that there is a portion of the filter 20 which portion is out of contact with a filter-supporting unit, namely that there is a space portion which encircles the filter, whereby hemocytes can be prevented from running along the filter-supporting unit, without passing through the filter, to flow into the electrode system.

Referring to FIG. 1 and FIG. 2, F1 designates cross-sectional area of the upstream side of the filter 20, while F2 designates cross-sectional area of the downstream side of the filter 20, the downstream side being positioned at the opening of the sample solution supply pathway. On the other hand, S1 designates cross-sectional area of the opening of the sample solution supply pathway, while S2 designates cross-sectional area of the sample solution supply pathway.

The present invention is to have a relation S1<F1. Thereby, plasma of a blood with the hemocytes thereof having been filtered out quickly reaches the electrode system. A preferable relation is S2≦F1, more preferably F2≦F1.

In order to measure a cholesterol level in a blood by using this sensor, a sample blood is to be supplied onto the recess 8 of the base plate 1 through the through-hole 28 of the cover 21. The here supplied blood penetrates into inside of the filter 20 from its end portion. The penetration speed of hemocytes of a blood in the filter 20 is slower than that of plasma, which is a liquid component. Therefore, the plasma seeps from the end, at the electrode system side, of the filter. The plasma having thus seeped therefrom fills whole of the sample solution supply pathway from the vicinity of the electrode system to the air vent 22 while dissolving the reaction reagent, which comprises e.g. enzymes and is carried at a position to cover the electrode system or at a rear surface of the cover right above the position. When the whole of the sample solution supply pathway is filled with the liquid, the flow of the liquid in the filter 20 stops. At this instant, the hemocytes do not reach the end portion, at the electrode system side, of the filter 20, and are retained at the positions then. Accordingly, the filter 20 is so designed as to make a difference in flow resistance between the plasma and the hemocytes to such extent that the hemocytes still do not reach the downstream side of the filter, even after the plasma of such an amount as to fill the whole of the sample solution supply pathway passes therethrough. A suitable filter according to the present invention is a depth filter having an average pore size of about 1 to 7 $\mu$m.

Figure 4:
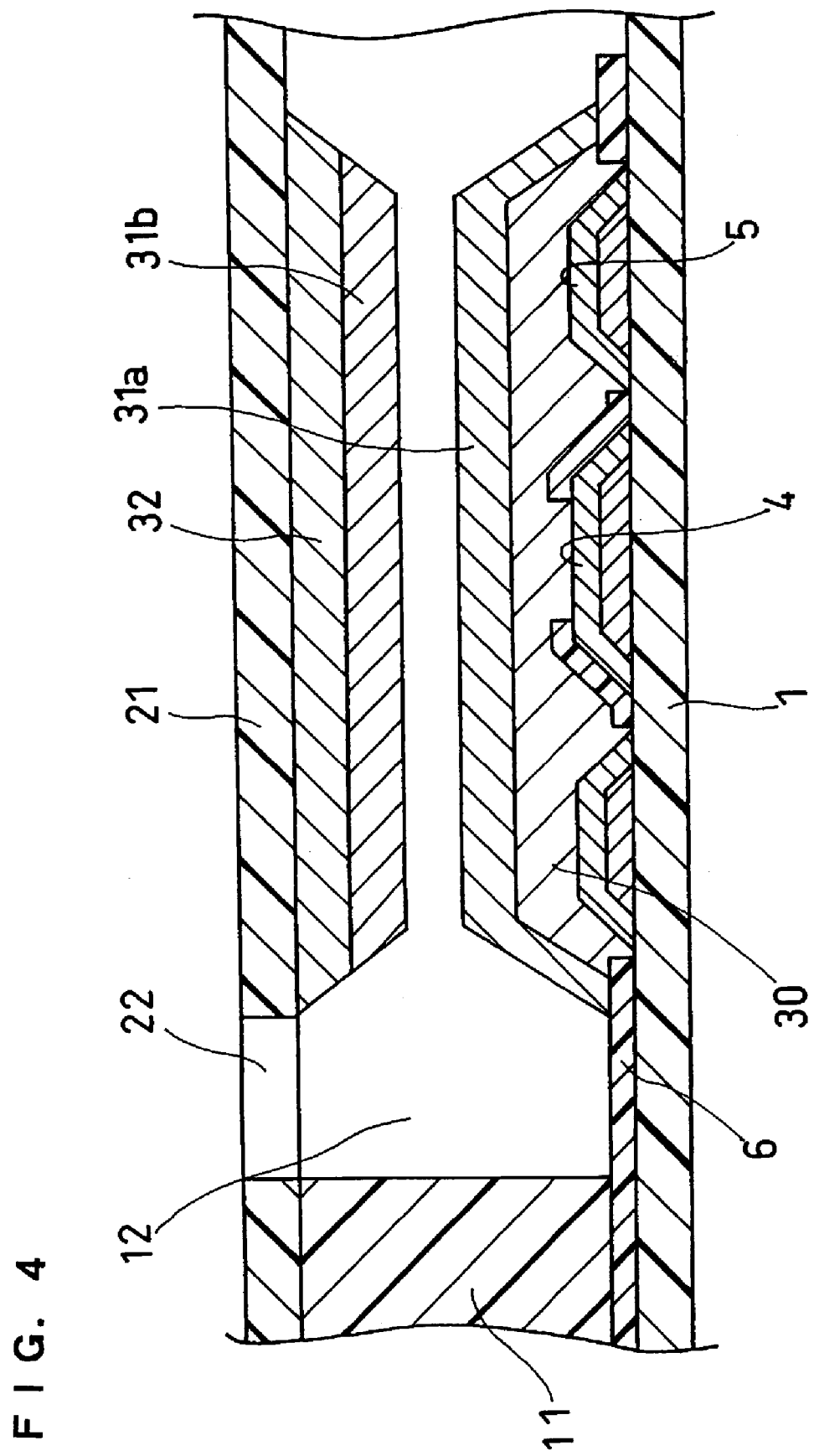
FIG. 4 is an enlarged cross-sectional view of a main part of the same sensor.

After such hemocyte filtering process, the reaction reagent dissolved by the plasma chemically reacts with a component, to be measured, in the plasma, the component being e.g. cholesterol in the case of a cholesterol sensor. After a given time passes thereafter, the component in the plasma can be quantified by measuring an electric current value based on electrode reaction. FIG. 4 shows an example of configuration of the reaction reagent layer in the vicinity of the electrode system at the sample solution supply pathway. On the electrode system on the base plate 1, a layer 30 of a sodium salt of carboxymethyl cellulose (hereafter simply referred to as CMC), which is a hydrophilic polymer, and a layer 31a of a reaction reagent containing e.g. an electron mediator are formed. Further, a surfactant layer 32 and a reaction reagent layer 31b containing an oxidoreductase are formed on a rear surface of the cover member having the cover 21 combined with the spacer 11, the rear surface being exposed to the sample solution supply pathway.

Figure 5:
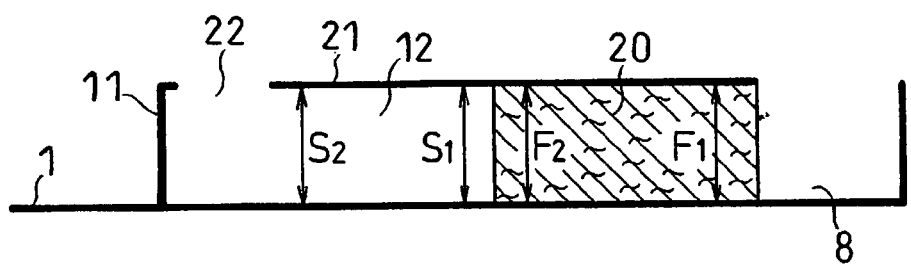
FIG. 5 is a schematic vertical cross-sectional view, showing examples of structures of sample supply units for a sensor.
Figure 5:
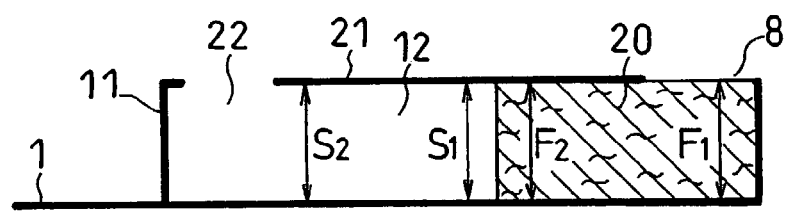
Figure 5:
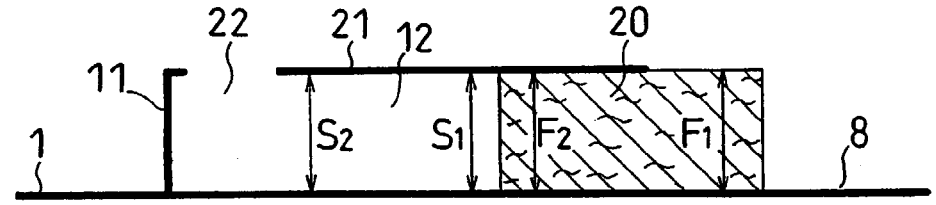
Figure 6:
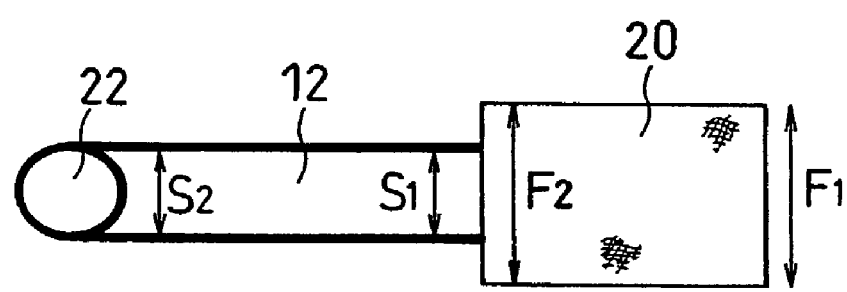
FIG. 6 is a schematic plan view, showing examples of modifications of filters for a sensor.
Figure 6:
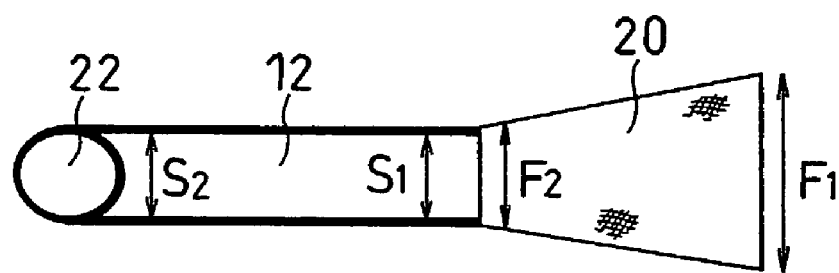
Figure 6:
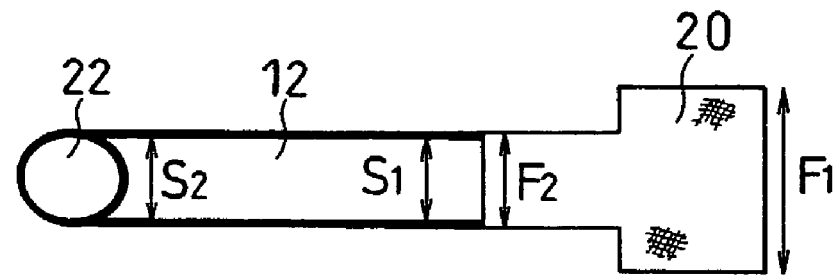
Figure 7:
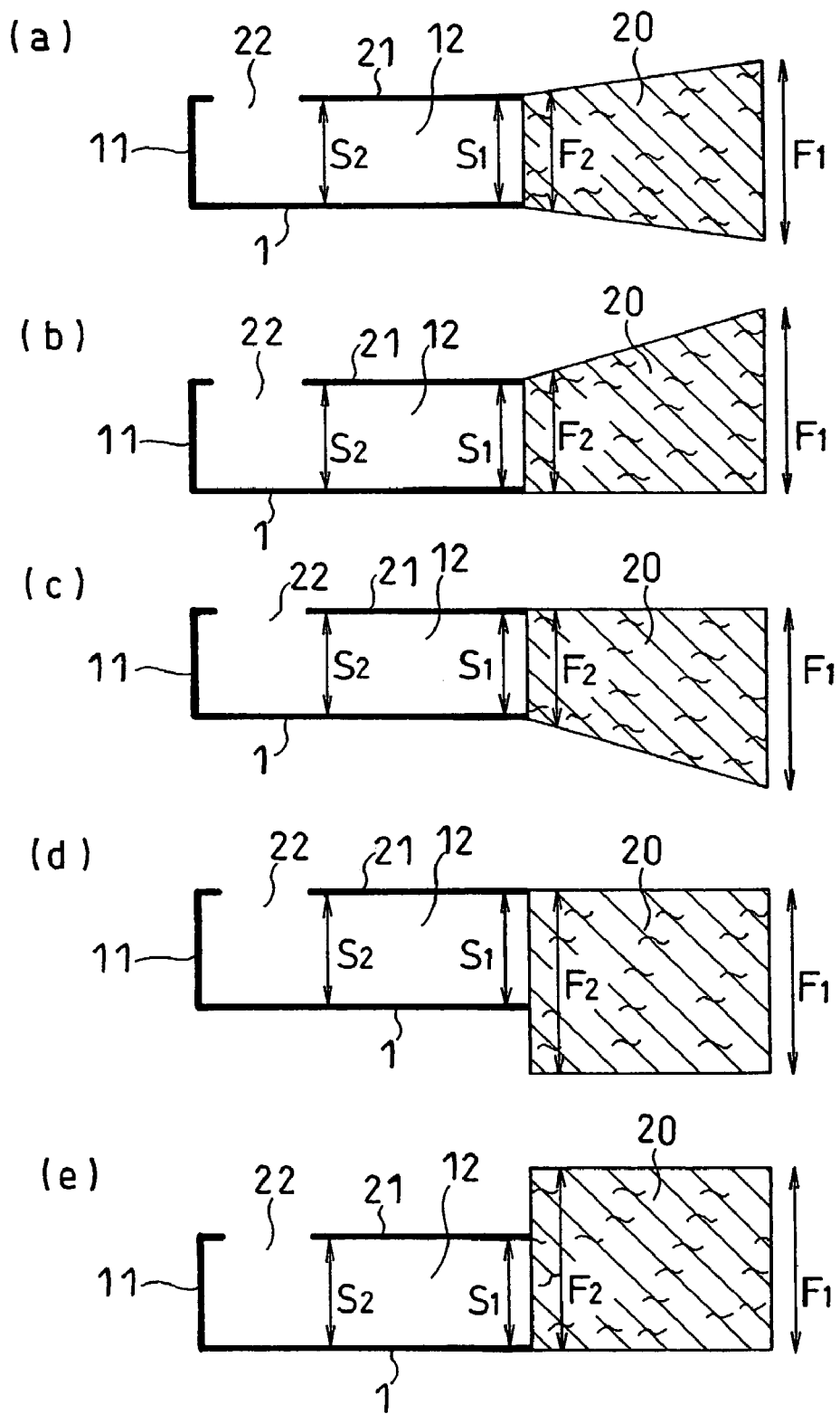
FIG. 7 is a schematic vertical cross-sectional view, showing examples of modifications of filters for a sensor.

FIGS. 5, 6 and 7 are schematic drawings, showing examples of modifications of the sensor.

FIG. 5 shows different examples of sample supply units. FIG. 5(a) shows a structure, in which a sample supply unit 8 has a recess to receive a sample solution as in FIG. 1. FIG. 5(b) shows an example having a sample supply unit 8 structured in a manner that the filter 20 has, at an upside of an end portion thereof, an exposed portion to which a sample solution is to be applied. FIG. 5(c) shows such a structure that an upside of an end portion of and the upstream side end surface of the filter 20 are exposed. Thus, a sample can be applied not only to the sample supply unit 8, but also to the upside of the end portion of the filter 20.

FIG. 6 is a plan view showing various shapes of filters. FIG. 6(a) shows an example, in which the filter has one same width from the upstream side to the downstream side thereof. FIG. 6(b) shows an example, in which the filter has a taper to have a width continuously decreasing from the upstream side to the downstream side thereof, the shape thereof thus being roughly trapezoidal. FIG. 6(c) shows an example, in which its width is so changed at a midpoint that the width at the upstream side is larger than that of the downstream side.

FIG. 7 shows examples of filters having different cross-sectional shapes. In FIGS. 7(a) to (c), such tapers are provided as to make the cross-sections of the upstream sides be larger than those of the downstream sides. In FIGS. 7(d) and (e), each upstream side has a cross-section the same as that of the downstream side.

As shown in FIG. 1 and FIGS. 5 to 7 above, the slit 12, which constitutes the sample solution supply pathway, is designed to have an area of cross-section, perpendicular to the direction for the liquid to flow in, smaller than the cross-sectional area of the filter 20 in each case. Further, the filter 20 is to have substantially a uniform density throughout of it. Thus, according to the present invention, the cross-sectional area S2 of the sample solution supply pathway is designed to be smaller than the cross-sectional area F1 of the upstream side of the filter 20, whereby the plasma of the blood with its hemocytes having been filtered out is quickly sucked into the sample solution supply pathway owing to capillary phenomena. By making smaller the cross-sectional area of the filter at a front end thereof, it becomes possible to allow the plasma to quickly flow into the inside of the sensor.

It also becomes possible to allow the plasma to quickly flow into inside of the sample solution supply pathway in the case that each sample supply unit as shown in FIG. 5 is combined with each plane shape of filter as shown in FIG. 6 and/or each cross-sectional shape of filter as shown in FIG. 7.

According to each such biosensor as shown, the width of the upstream side of a filter is preferred to be not larger than 5 mm, and the thickness thereof to be not larger than 2 mm. The width of the opening of the sample solution supply pathway is preferred to be not larger than 2 mm, and the thickness thereof to be not larger than 200 $\mu$m.

Figure 8:
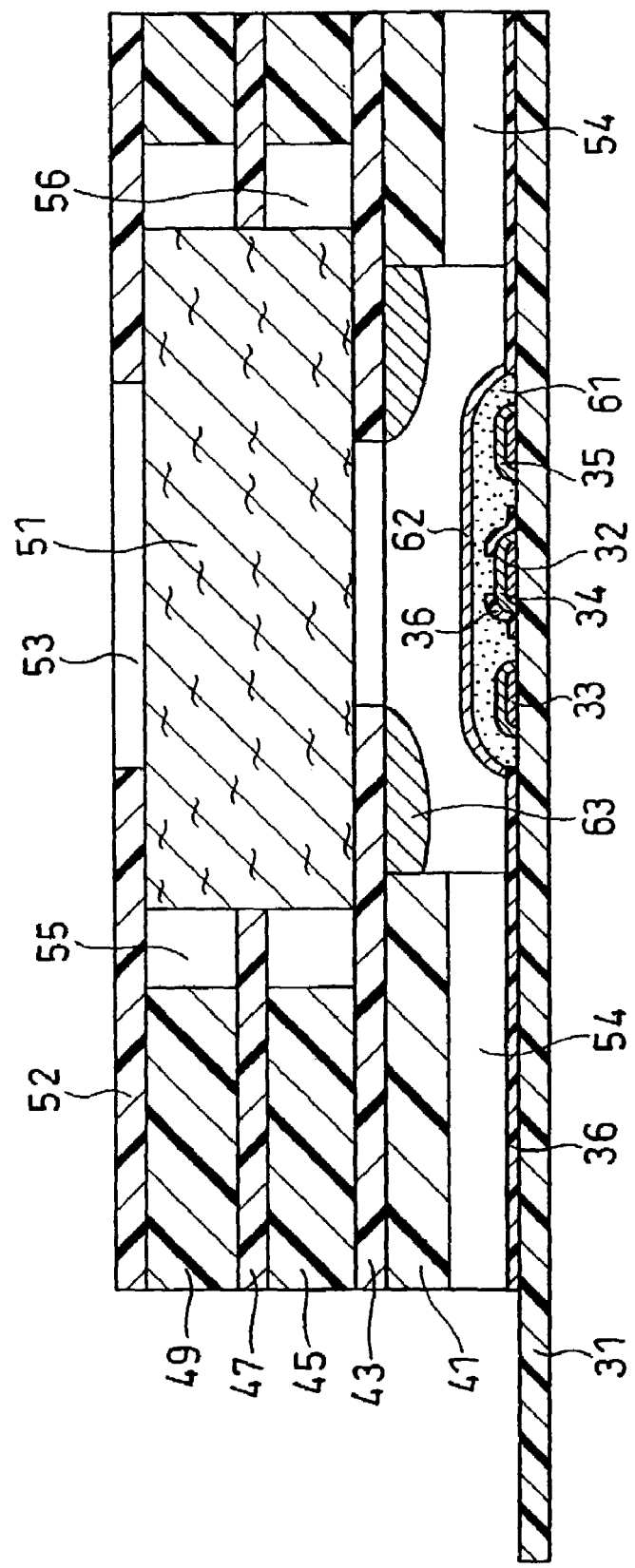
FIG. 8 is a vertical cross-sectional view of a sensor according to another embodiment mode of the present invention.
Figure 9:
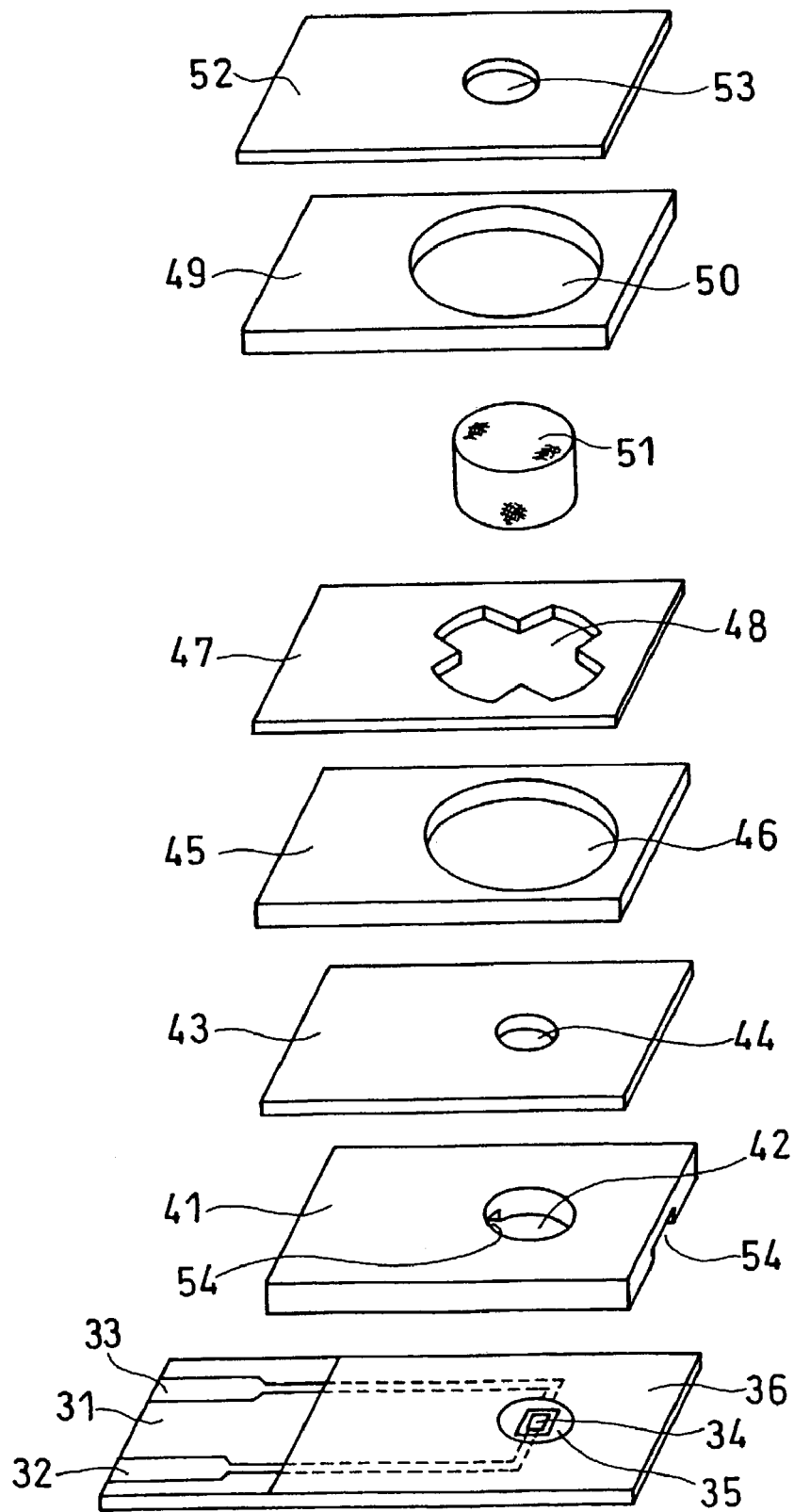
FIG. 9 is an exploded oblique view of the same sensor.

FIG. 8 is a vertical cross-sectional view of a biosensor according to another embodiment mode of the present invention, while FIG. 9 is an exploded oblique view with a reagent layer thereof having been removed.

On an insulating base plate 31 are formed leads 32 and 33, a working electrode 34 and a counter electrode 35 connected to the respective leads as well as an insulating layer 36 in a manner similar to the case of FIG. 1. Plural spacers 41, 43, 45, 47 and 49 and a cover 53 are assembled on this base plate 31. A filter 51 is set at a section of through-holes 46, 48 and 50 between the spacer 43 and the cover 53. A through-hole 53 of the cover 52 constitutes a sample solution supply pathway, and through-holes 42 and 44 provided in the spacers 41 and 43 constitute a sample solution supply pathway. The through-holes 46 and 50 of the spacers 45 and 49 are larger in diameter than the filter 51, so that spaces as designated by reference numerals 55 and 56 is formed around the filter 51 to encircle the filter 51. The spacer 47 partially contacts with an outer periphery of the filter 51 to function to position the filter. The spacer 41 has a pair of air vents 54 for releasing a terminal end portion side of the sample solution supply pathway to outside atmosphere. Thus, owing to capillary phenomena, a sample solution is introduced into the filter 51 and the sample solution supply pathway in a region spanning from the through-hole 53, which serves as a sample supply unit, to the electrode system. The movement of the sample solution stops when plasma filtrated by the filter 51 reaches the electrode system.

Here, each thickness of the spacers 49 and 45, which define heights of spaces 55 and 56, is preferred to be not smaller than 100 μm. The spacer 41 has the through-hole 42, which serves as a place where to react the sample solution with the reagent. The thickness of the spacer 41 is preferred to be not larger than 200 μm.

In this example, a CMC layer 61 and an electron mediator layer 62 are formed on the electrode system, and a layer 63 containing an enzyme and a surfactant is formed on a rear surface of the spacer 43.

Figure 10:
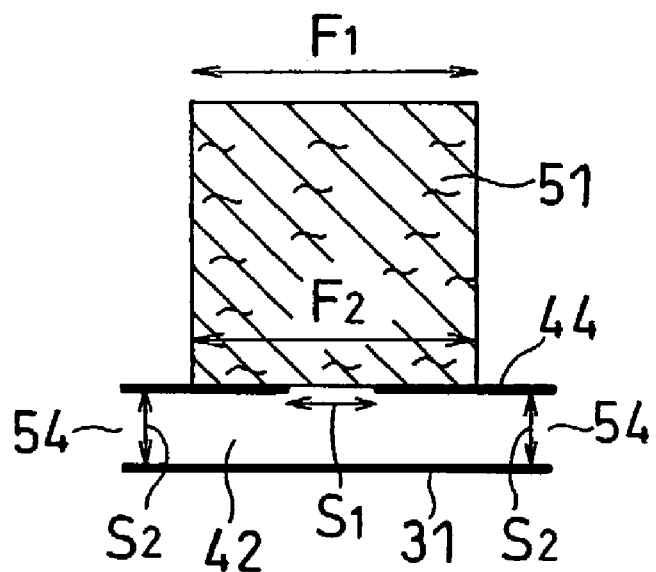
FIG. 10 is a schematic vertical cross-sectional view, showing examples of modifications of filters for a sensor.
Figure 10:
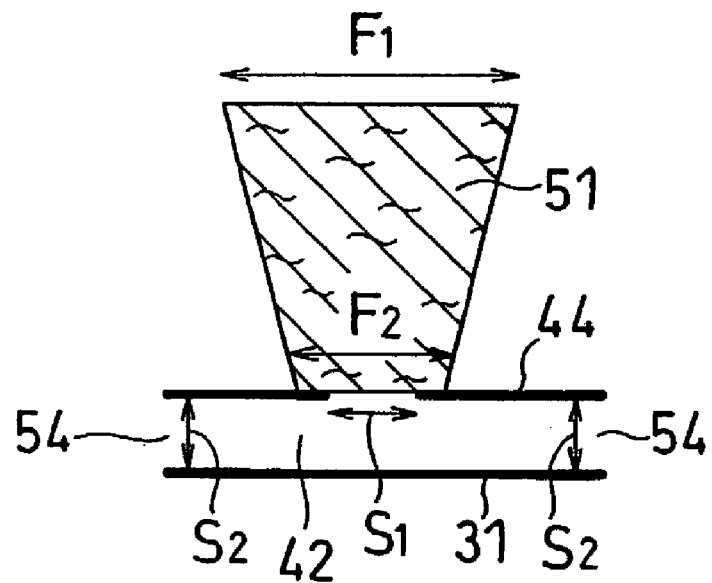

FIG. 10 shows examples of filters in sensors of such type that as described above, a sample solution is supplied, from a sample supply unit provided at a cover side, toward an electrode system in the direction of gravity. FIG. 10(a) shows an example using a filter 51 having one same cross-section at both upstream side and downstream side thereof in the same manner as in FIG. 8, whereas FIG. 10(b) shows an example having, at the downstream side thereof, a cross-sectional area smaller than a cross-sectional area at the upstream side thereof.

Hereinafter, an Example of the present invention will be described.

EXAMPLE 1

A method of making a cholesterol sensor will be described below, which has a structure as shown in FIGS. 1 to 4, in which: a reaction layer 31a contains an electron mediator; a reaction layer 31b contains cholesterol oxidase, cholesterol esterase and a surfactant; and a layer 32 comprises a surfactant.

Firstly, 5 μl of an aqueous solution containing 0.5 wt % of sodium salt of carboxylmethyl cellulose was dropped onto an electrode system, and was then dried in a hot air drier of 50° C. for 10 minutes, whereby a CMC layer 30 was formed. Next, 4 μl of an aqueous solution of potassium ferricyanide (corresponding to 70 mM of potassium ferricyanide) was dropped onto the CMC layer 30, and was then dried in a hot air drier of 50° C. for 10 minutes, whereby a reaction layer 31a containing potassium ferricyanide was formed.

An ethanol solution in an amount of 2 μl containing 2 wt % of polyoxyethylene(10)octylphenyl ether (Triton X-100), which is a surfactant, was dropped onto a recess formed by a slit of a cover having a cover combined with a spacer, and was dried at room temperature for 3 minutes, whereby a surfactant layer 32 was formed. The above-described slit had a width of 2 mm and a length of 4.5 mm, while the spacer had a thickness of 100 μm.

Polyoxyethylene(10)octylphenyl ether (Triton X-100), which is a surfactant, was added to an aqueous solution having dissolved therein cholesterol oxidase originating from Nocardia (EC1.1.3.6, hereafter referred to as ChOD) and cholesterol esterase originating from Pseudomonas (EC. 3.1.1.13, hereafter referred to as ChE). This mixed aqueous solution in an amount of 1.5 μl was dropped onto the surfactant layer 32, and was frozen by liquid nitrogen of −196° C., and was then stored in Kjeldahl flask and then dried in a freeze-drier overnight, thereby to form a reaction layer 31b, containing 480 units (U)/ml of cholesterol oxidase, 1,200 U/ml of cholesterol esterase and 2 wt % of surfactant. On the thus made base plate 1 for a sensor, a glass fiber filter paper having been cut to have a trapezoid shape having an upper side of 2 mm, a lower side of 4 mm and a height of 3 mm and to have a thickness of 600 μm and an average pore size of 2.3 μm was so provided as not to contact with a working electrode in a manner as shown in FIG. 2.

Thereafter, the above-described cover member was bonded to the base plate, whereby a cholesterol sensor as shown in FIG. 1 was made.

COMPARATIVE EXAMPLE 1

Figure 11:
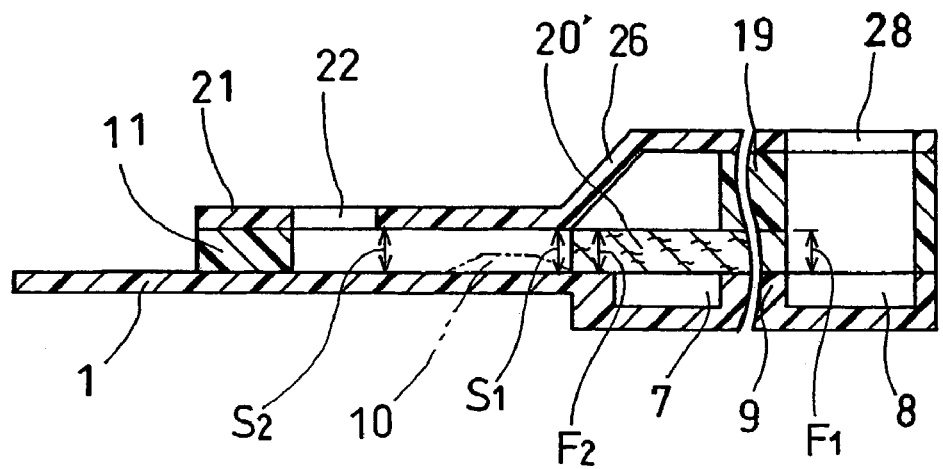
FIG. 11 is a vertical cross-sectional view of a sensor according to a Comparative Example.
Figure 12:
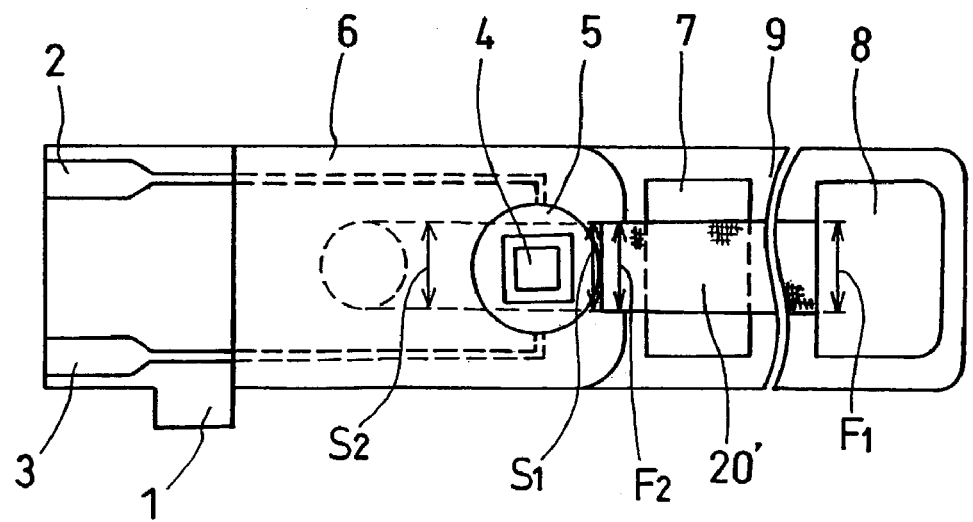
FIG. 12 is a plan view of the same sensor.

A cholesterol sensor similar to that of Example 1 was assembled, except that the sensor here employed a filter 20' having such dimensions that its width was 2 mm, its length was 27 mm, and its thickness was 100 μm as shown in FIG. 11 and FIG. 12.

The cholesterol sensors A and B according to Example 1 and Comparative Example, respectively, were each provided with 20 μl of a whole blood as a sample solution, which was introduced into the recess 8 of the base plate 1 through the through-hole 28 of the cover 21, the through-hole being an inlet for the sample solution. At a time point of 3 minutes thereafter, a pulse voltage of +0.5 V toward anode direction was applied to the measuring electrode with the counter electrode being as a reference, wherein a value of an electric current flowing, at a time point of 5 seconds after the pulse voltage application, between the working electrode and the counter electrode was measured. The results of such measurements are shown in FIG. 13. Each of both filters in Example 1 and Comparative Example 1 had an apparent volume of about 5.4 mm$^3$.

As apparent from the graph, according to a sensor of the present invention, a good linearity can be obtained between the cholesterol concentrations and the response values.

Industrial Applicability

According to the present invention, hemocytes of a blood, which are obstructing substances, can be removed by a filter, and the blood can be quickly supplied to the electrode system, so as to be able to provide an electrochemical biosensor having superior response characteristics.

What is claimed is:

1. A biosensor comprising: an insulating base plate; an electrode system having a measuring electrode and a counter electrode provided on said base plate; a reaction layer comprising at least an oxidoreductase and an electron mediator; a sample solution supply pathway including said electrode system and said reaction layer; a sample supply unit; and a filter provided between said sample supply unit and said sample solution supply pathway for filtering out hemocytes of a blood, wherein plasma of said blood, with said hemocytes having been filtered out by said filter, is sucked into the inside of said sample solution supply pathway owing to capillary phenomena, wherein said filter has, at an upstream side thereof, a cross-sectional area larger than a cross-sectional area of an opening of said sample solution supply pathway, and also larger than a cross-sectional area at a downstream side thereof, said downstream side being positioned at said opening of said sample solution supply pathway.

2. The biosensor according to claim 1, wherein said sample solution supply pathway has a cross-sectional area equal to or smaller than said cross-sectional area of said opening of said sample solution supply pathway.

3. The biosensor according to claim 1, wherein said cross-sectional area of said filter at said downstream side is equal to or larger than said cross-sectional area of said opening of said sample solution supply pathway.

4. The biosensor according to claim 1, wherein said filter comprises a porous body having pores interconnected in a three-dimensional manner, and wherein said porous body moves said blood, owing to capillary action, from a sample supply unit side to a sample solution supply pathway side, and has a function to filter out said hemocytes owing to differences in flow resistances between said plasma and said hemocytes.

5. The biosensor according to claim 1, which comprises, at a portion of said filter in a region spanning from said sample supply unit to said sample solution supply pathway, a space encircling a surface of said filter.

6. The biosensor according to claim 1, wherein a front end of said filter at a downstream side thereof is out of contact with said electrodes.

7. The biosensor according to claim 1, wherein said sample solution supply pathway is formed between said base plate and a cover member combined with said base plate.

8. The biosensor according to claim 7, wherein at least a portion of said cover member, which portion covers said filter and said sample solution supply pathway, is transparent.

9. The biosensor according to claim 7, wherein a surfactant is carried or fixed on said cover member.

* * * * *